US010385311B2

(12) United States Patent
Neu et al.

(10) Patent No.: US 10,385,311 B2
(45) Date of Patent: Aug. 20, 2019

(54) METHOD OF MAKING BIOLOGICAL TISSUE COMPONENTS

(71) Applicant: PURDUE RESEARCH FOUNDATION, West Lafayette, IN (US)

(72) Inventors: Corey Philip Neu, Boulder, CO (US); Tyler Anthony Novak, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 147 days.

(21) Appl. No.: 15/167,132

(22) Filed: May 27, 2016

(65) Prior Publication Data

US 2016/0376551 A1 Dec. 29, 2016

Related U.S. Application Data

(60) Provisional application No. 62/167,237, filed on May 27, 2015.

(51) Int. Cl.
*C12N 5/00* (2006.01)
*A61L 27/58* (2006.01)

(52) U.S. Cl.
CPC ........... *C12N 5/0081* (2013.01); *A61L 27/58* (2013.01); *C12N 2533/90* (2013.01)

(58) Field of Classification Search
None
See application file for complete search history.

(56) References Cited

U.S. PATENT DOCUMENTS

| | | | | |
|---|---|---|---|---|
| 7,534,449 | B2 * | 5/2009 | Saltzman | A61K 9/0019 424/417 |
| 2004/0059430 | A1 * | 3/2004 | Kim | A61L 27/3604 623/23.72 |
| 2005/0256588 | A1 * | 11/2005 | Sawa | A61L 27/3804 623/23.72 |
| 2006/0002852 | A1 * | 1/2006 | Saltzman | A61K 9/0019 424/1.11 |
| 2011/0195107 | A1 * | 8/2011 | Min | A61L 27/3604 424/423 |
| 2015/0216812 | A1 * | 8/2015 | Machluf | A61K 9/5015 424/499 |

OTHER PUBLICATIONS

P. M. Crapo et al., an Overview of Tissue and Whole Organ Decellularization Processes, Biomaterials, 2011, pp. 3233-3243, vol. 32, Elsevier Ltd., US.
Y. L. Yang et al., Influence of Chondroitin Sulfate and Hyaluronic Acid on Structure, Mechanical Properties, and Glioma Invasion of Collagen I Gels, Biomaterials, 2011, pp. 7932-7940, vol. 32, Elsevier Ltd., US.
B. D. Elder et al., Extraction Techniques for the Decellularization of Tissue Engineered Articular Cartilage Constructs, Biomaterials, 2009, pp. 3749-3756, vol. 30, US.
N. C. Cheng et al., Chondrogenic Differentiation of Adipose-Derived Adult Stem Cells by a Porous Scaffold Derived from Native Articular Cartilage Extracellular Matrix, Tissue Engineering: Part A, 2009, pp. 231-241, vol. 15, Mary Ann Libert, Inc., US.
B. O. Diekman et al., Chondrogenesis of Adult Stem Celss from Adipose Tissue and Bone Marrow: Induction by Growth Factors and Cartilage-Derived Matrix, Tissue Engineering: Part A, 2010, pp. 523-533, vol. 16, Mary Ann Liebert, Inc., US.
C. C. Chen et al., Cartilage Fragments from Osteoarthritic Knee Promote Chondrogenesis of Mesenchymal Stem Cells without Exogenous Growth Factor Induction, Journal of Orthopaedic Research, Mar. 2012, pp. 393-400, vol. 30, Wiley Periodicals, Inc., US.
T. Novak, et al., Cell Encapsulation in a Magnetically Aligned Collagen-GAG Copolymer Microenvironment, Acta Biomaterialia, 2015, pp. 274-282, vol. 11, Elsevier Ltd., US.
G. M. Genin et al., Functional Grading of Mineral and Collagen in the Attachment of Tendon to Bone, Biophysical Journal, Aug. 2009, pp. 976-985, vol. 97, Biophysical Society, US.
X. L. Lu et al., A Linearized Formulation of Triphasic Mixture Theory for Articular Cartilage, and Its Application to Indentation Analysis, Journal of Biomechanics, 2010, pp. 673-679, vol. 43, Elsevier Ltd., US.
M. B. Keogh et al., Sustrate Stiffness and Contracile Behaviour Modulate the Functional Maturation of Osteoblasts on a Collagen GAG Scaffold, Acta Biomaterials, 2010, pp. 4305, vol. 6.
J. L. Bailey et al., Collagen Oligomers Modulate Physical and Biological Properties of Three-Dimensional Self-Assembled Matrices, Biopolymers, 2011, pp. 77-93, vol. 95, Wiley Periodicals, Inc., US.
T. K. Sampath et al., Dissociative Extraction and Reconstitution of Extracellular Matrix Components Involved in Local Bone Differentiation, National Academy Science USA, Dec. 1981, pp. 7599-7603, vol. 78, No. 12.
A. Didangelos et al., Extracellular Matrix Composition and Remodeling in Human Abdominal Aortic Aneurysms: A Proteomics Approach, Molecular & Cellular Proteomics, 2011, vol. 10, The American Society for Biochemistry and Molecular Biolog, Inc., US.
S. T. Kreger et al., Polymerization and Matrix Physical Properties as Important Design Considerations for Soluble Collagen Formulations, Biopolymers, Aug. 2010, pp. 690-707, vol. 93, Wiley Periodicals, Inc., US.

(Continued)

*Primary Examiner* — Blaine Lankford
(74) *Attorney, Agent, or Firm* — Maginot, Moore & Beck LLP

(57) ABSTRACT

A method of preparing a biological composite matrix system includes combining tissue microparticles with a curable medium. The tissue microparticles are formed by pulverizing tissue, sorting the pulverized tissue particles, and decellularizing the pulverized tissue particles. The tissue microparticles are then mixed with the curable medium and the resulting composite is cured to form a microparticle-medium composite matrix. The microparticle-medium composite matrix is compressed to increase the strength of the matrix and to increase the density of the microparticles to a predetermined density.

13 Claims, 13 Drawing Sheets
Specification includes a Sequence Listing.

(56) References Cited

OTHER PUBLICATIONS

M. Doube et al., BoneJ: Free and Extensible Bone Image Analysis in ImageJ, Bone, 2010, pp. 1076-1079, vol. 47, US.

M. E. Joyce et al., Transforming Growth Factor-B and the Initiation of Chondrogenesis and Osteogenesis in the Rat Femur, The Journal of Cell Biology, Jun. 1990, pp. 2195-2207, vol. 110, The Rockefeller University Press, US.

S. D. Thorpe et al., The Response of Bone Marrow-Derived Mesenchymal Stem Cells to Dynamic Compression Following TGF-beta3 Induced Chondrogenic Differentiation, Annals of Biomedical Engineering, 2010, pp. 2896-2909, vol. 38, Royal College of Surgeons in Ireland.

Schwarz, S., et al., Decellularized Cartilage Matrix as a Novel Biomatrix for Cartilage Tissue-Engineering Applications, Tissue Eng Part A, 2012, pp. 2195-2209, vol. 18.

Kang, H., et al., In vivo cartilage repair using adipose-derived stem cell-loaded decellularized cartilage ECM scaffolds, Journal of Tissue Engineering and Regenerative Medicine, 2014, pp. 442-453, vol. 8, Wiley Online Library.

Xue, J., et al., Chondrogenic Differentiation of Bone Marrow-Derived Mesenchymal Stem Cells Induced by Acellular cartilage sheets, Biomaterials 2012, pp. 5832-5840, vol. 33, Elsevier Ltd.

Yang, Q., et al., A Cartilage ECM-Derived 3-D Porous Acellular Matrix Scaffold for In Vivo Cartilage Tissue Engineering with PKH26-Labeled Chondrogenic Bone Marrow-Derived Mesenchymal Stem Cells, Biomaterials, 2008, pp. 2378-2387, vol. 29, Elsevier Ltd.

Chang, C. H., et al., Human Acellular Cartilage Matrix Powders as a Biological Scaffold for Cartilage Tissue Engineering with Synovium-Derived Mesenchymal Stem Cells, Journal of Biomedical Materials Research A, 2014, pp. 2248-2257, vol. 102, Issue 7, Wiley Online Library.

Mow, V. C., et al., Cartilage and Diarthrodial Joints as Paradigms for Hierarchical Materials and Structures, Biomaterials, 1992, pp. 67-97, vol. 13, No. 2, Butterworth-Heinemann Ltd.

Peretti, G. M., et al., Bonding of Cartilage Matrices with Cultured Chondrocytes: An Experimental Model, Journal of Orthopaedic Research, 1998, pp. 89-95 vol. 16, No. 1, The Journal of Bone and Joint Surgery, Inc.

Peretti, G. M., et al., Cell-Based Tissue-Engineered Allogeneic Implant for Cartilage Repair, Tissue Engineering, 2000, pp. 567-576, vol. 6, No. 5, Mary Ann Liebert, Inc.

Benders, K. E., et al., Extracellular Matrix Scaffolds for Cartilage and Bone Regeneration, Trends in Biotechnology, 2013, pp. 169-176, vol. 31, No. 3, Elsevier Ltd.

Novak, T., et al., Mechanisms and Microenvironment Investigation of Cellularized High Density Gradient Collagen Matrices via Densification, Advanced Functional Materials, 2016, pp. 2617-2628, vol. 26, Wiley Online Library.

Pepinsky, R.B., Selective Precipitation of Proteins from Guanidine Hydrochloride-Containing Solutions with Ethanol, Analytical Biochemistry, 1991, pp. 177-181, vol. 195, Academic Press, Inc.

* cited by examiner

METHOD OF MAKING BIOLOGICAL TISSUE COMPONENTS

PRIORITY CLAIM

This application claims priority to U.S. Provisional Patent Application No. 62/167, 237, entitled "Tissue Engineering Composites," and filed on May 27, 2015, the specification of which is hereby incorporated by reference in its entirety.

BACKGROUND

The selective growth and generation of biological tissue is an area of biomedical scientific and technological advancement with a variety of useful applications. For example, selectively grown or generated biological tissue can be implanted into living beings to repair or replace biological tissue that has been damaged or lost due to injury or illness. Connective tissue, muscle tissue, nervous tissue, and epithelial tissue compose the organs and body structures of living beings, and the ability to selectively generate any or all of these tissue types for implantation and repair or replacement is desirable. However, it is extremely difficult to generate any tissue which perfectly mimics the biological and mechanical characteristics of the target tissue and to generate a tissue which the body will not reject as foreign upon implantation.

One method for selectively generating biological tissue to be implanted in a living being includes generating a portion of donor tissue that is similar or nearly identical to the tissue to be repaired and/or replaced, also referred to herein as "native" tissue. In some cases, the implanted tissue is nearly identical to the native tissue. In other cases, however, the implanted tissue is a precursor to the native tissue, and the implanted tissue serves as a scaffold for the further generation and integration of the native tissue within the body. In these latter cases, the implanted tissue must enable and facilitate growth and integration into existing tissue in the body. In either case, the implant tissue must enable and facilitate integration into the body and prevent rejection.

Generating tissue for implantation often includes decellularization of donor tissue to remove cellular and genetic material from the tissue. Decellularization can be achieved, for example, by applying a chemical decellularizing agent to the tissue. Decellularized tissue is beneficial because it contains the mature, healthy extracellular matrix (ECM) of the target tissue being repaired or replaced. Thus, native decellularized ECM is able to direct host cell infiltration, migration, and phenotype induction to promote integration of the implant tissue with the target tissue. Furthermore, the biological makeup of ECM components of various decellularized tissues is largely conserved and largely non-immunogenic. Thus, autologous, allogenic, and xenogenic transplantation of decellularized tissues with relatively minimized risk to the host is possible.

The efficacy of a decellularizing agent in producing acceptable decellularized tissue depends, in part, on the physical properties of the tissue being decellularized. For example, cartilage, and in particular articular cartilage, is generally composed of thick and dense tissue. Accordingly, the infiltration and/or penetration of decellularizing agents into the tissue, and thus the production of acceptable decellularized tissue, is inhibited by the structure of the tissue. Furthermore, after decellularization, the high tissue density of articular cartilage prevents cellular infiltration and remodeling in the long term, thus inhibiting integration of the implanted tissue. However, despite these challenges, generation and implantation of articular cartilage tissue is highly desirable, because articular cartilage is resilient to natural repair and is subject to high mechanical forces, which promotes further tissue degeneration.

Accordingly, methods have been developed to address the reduced cellular infiltration and remodeling of implant articular cartilage tissue. For example, in some methods, the ECM of the decellularized articular cartilage tissue is modified by guanidine-hydrochloride reduction of glycosaminoglycans (GAGs) to increase tissue porosity. However, such modifications to the ECM are often unsuccessful in promoting bulk cellular infiltration, which can lead to global degeneration and limited utility of the implant in the body.

Thus, further methods have been developed to help retain the local mechanical, structural, and biochemical microenvironment of native articular cartilage, but allow for easier penetration of decellularization agents as well as means to increase cellular infiltration into dense native tissue. For example, in some methods, atomized (e.g. pulverized or microparticulated) cartilage tissue is size controlled to create a powder of fragments of cartilage. Fragments are then either crosslinked to each other or suspended in a polymerizable medium to create three-dimensional constructs of tunable size and/or cartilage microparticle density, which can promote cell attachment and upregulation of cartilage specific genes (e.g. type II collagen, SOX9, aggrecan) to form neocartilage.

However, one problem with these methods is that crosslinking the fragments often requires conditions which are hostile to the tissue. Thus, cell-seeding, to add necessary cellular material back to the tissue, may be required after crosslinking. Cell-seeding is generally an imprecise and inefficient process, and usually results in cells that are not globally distributed in the three-dimensional construct. An additional problem with these methods is that they result in cartilage microparticle density that is largely dependent on the packing efficiency of the particles, but is otherwise uncontrolled. Furthermore, these methods do not facilitate investigation of the contribution of physiochemical properties to chondrogenic induction and maintenance, which could provide insight and direction to further improve selective tissue generation and integration. Thus, there remains a need to (1) create a more tunable, controlled system of cartilage microparticle construct formation without the need for hostile crosslinking, and (2) further examine the contribution of the complex native cartilage microenvironment to the induction of chondrogenic differentiation.

SUMMARY

Embodiments disclosed herein address one or more of the above observed needs.

A composite matrix system of decellularized tissue microparticles suspended in a medium matrix has been developed to address limitations of whole decellularized articular cartilage. The composite matrix system is plastically compressed such that the decellularized tissue microparticles reach a controlled, predetermined density near physiological levels. This composite matrix system can be used to investigate contributions of GAGs and collagenous components to chondrogenic induction and matrix properties.

More specifically, a method of making a composite matrix system having a predetermined density of biological tissue microparticles has been developed. The method includes decellularizing the tissue microparticles to remove cellular and genetic material, mixing the decellularized tissue microparticles into a medium to form a medium-tissue microparticle composite, and compressing the medium-tissue microparticle composite to form the composite matrix having the predetermined density of tissue microparticles.

Additionally, a method of making a biological tissue composite has also been developed. The method includes pulverizing the biological tissue into tissue microparticles, decellularizing the tissue microparticles to remove cellular and genetic material, mixing the decellularized tissue microparticles into a medium to form a medium-tissue microparticle composite, and compressing the medium-tissue microparticle composite to form the composite matrix having the predetermined density of tissue microparticles.

The above described features and advantages, as well as others, will become more readily apparent to those of ordinary skill in the art by reference to the following detailed description and accompanying drawings.

DETAILED DESCRIPTION

As described in more detail below, a method of making a composite matrix system having a predetermined density of biological tissue microparticles includes decellularizing microparticles, isolating and reducing the decellularized microparticles, and forming dense medium-microparticle composite matrices. The resulting composite matrices provide a tunable system, which enables investigation of the contribution of native microenvironments to tissue differentiation.

More specifically, in the case of articular cartilage tissue, the tunable system includes decellularized cartilage microparticles and a polymerizable collagen matrix, which form a composite material. Densifying or compressing the composite material increases the strength of the collagen matrix and increases the packing and spacing of the cartilage microparticles to a controlled level. Additionally, adding a series of guanidine reduction and mechanical reconstitution mixes of cartilage microparticles enables investigation of the contribution of covalently bound GAGs and the structural, collagenous ECM.

While the embodiments described below pertain to cartilage microparticles in a collagen matrix, the method and analysis are applicable to other biological tissues and matrix materials. For example, microparticles formed from tissue containing osteoblast cells, chondrocyte cells, myocyte cells, fibrocartilage cells, bladder cells, intestine cells, liver cells, kidney cells, skin cells, lung cells, gastrointestinal cells, or neural cells can be included in the composite matrix instead of cartilage. Additionally, matrix material formed from, for example, gelatin, silk, agarose, polypropylene glycol alginate (PGA), polylactic acid (PLA), polylactic-co-glycolic acid (PLGA), or polyvinyl acetate (PVA) can be included in the composite matrix instead of collagen.

Figure 1:
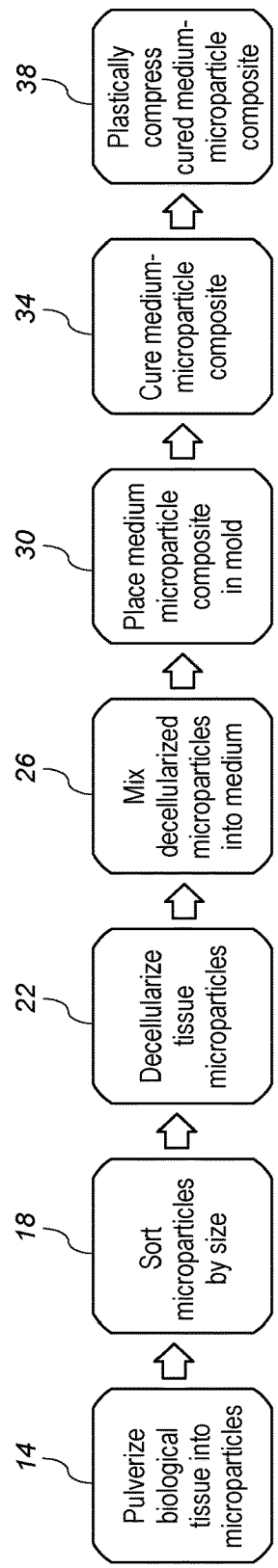
FIG. 1 depicts a method of making a composite matrix system having a predetermined density of biological tissue microparticles.

FIG. 1 depicts a method 10 of making a composite matrix system having a predetermined density of biological tissue microparticles. The method 10 includes pulverizing biological tissue into microparticles (step 14), sorting the microparticles into a plurality of groups by size (step 18), decellularizing at least one of the groups of microparticles (step 22), mixing the decellularized microparticles into a curable medium (step 26), placing the medium-microparticle composite into a mold (step 30), curing the medium-microparticle composite in the mold (step 34), and plastically compressing the cured medium-microparticle composite (step 38) to form a microparticle-medium composite matrix system having a predetermined density of the biological tissue microparticles.

Figure 2A:
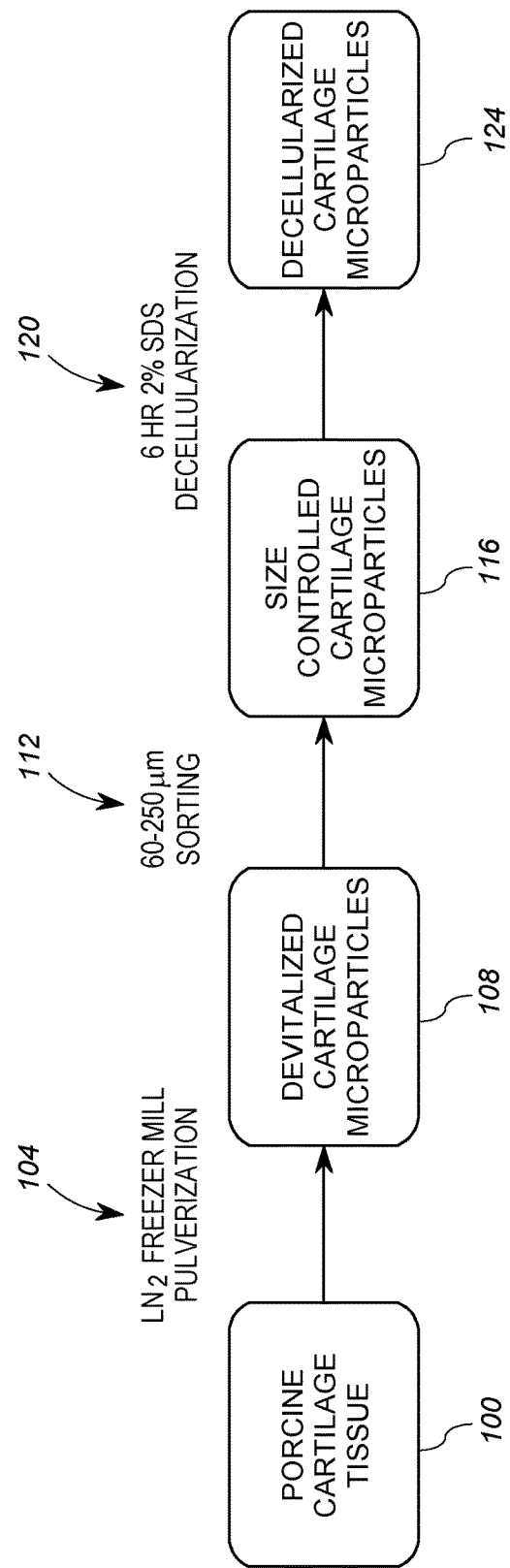
FIG. 2A depicts a method of forming decellularized microparticles.
Figure 2B:
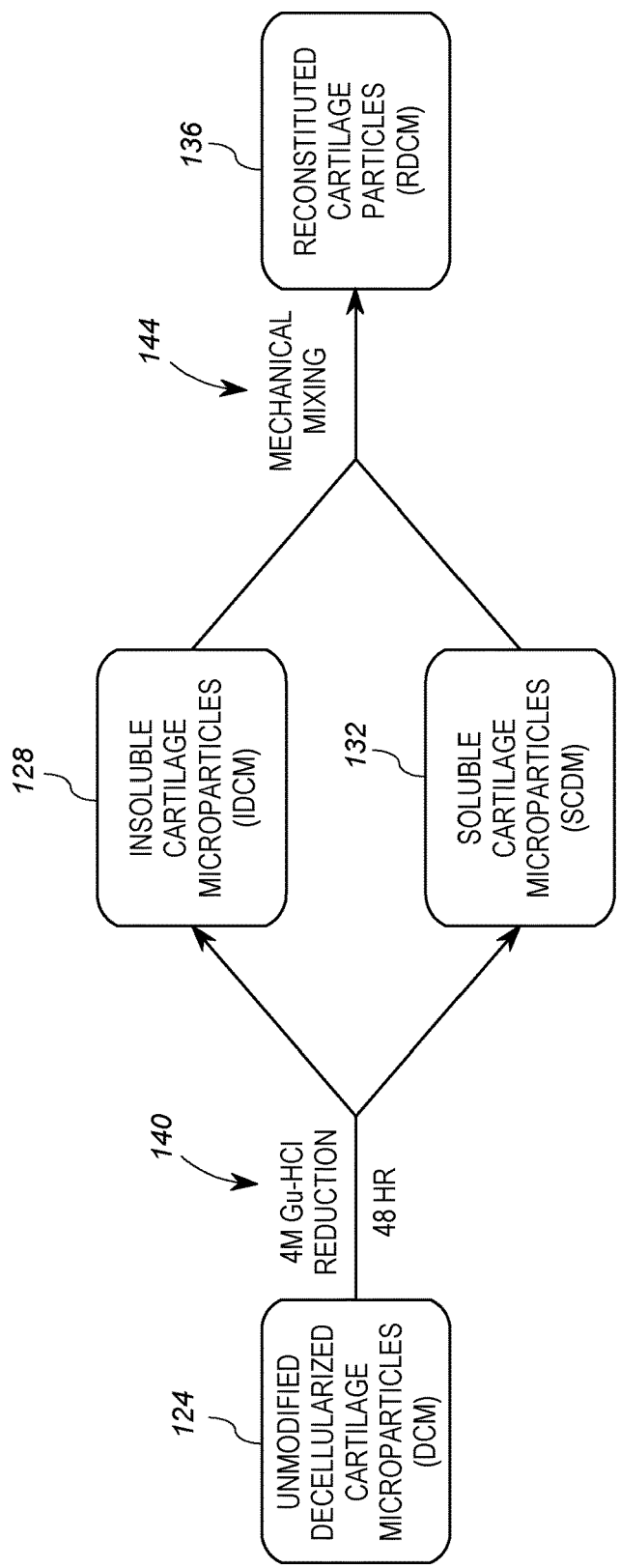
FIG. 2B depicts a method of forming different groups of the decellularized microparticles of FIG. 2A.
Figure 2C:
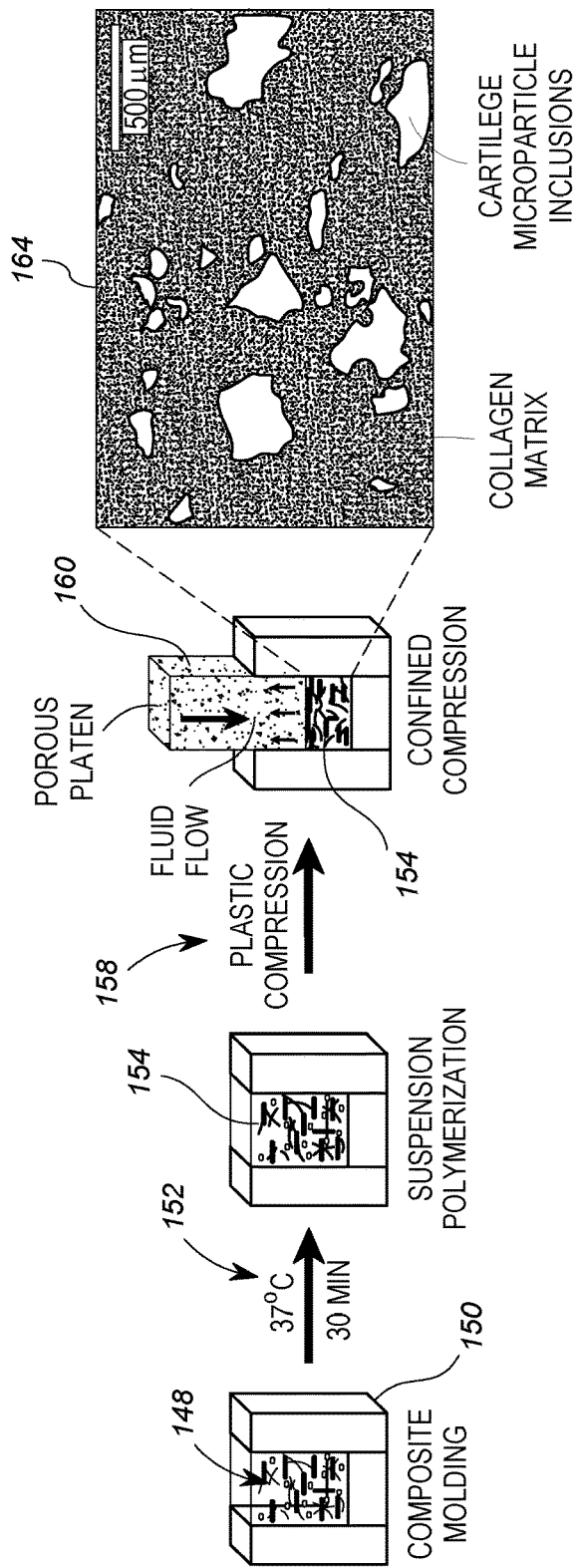
FIG. 2C depicts a method of forming a composite matrix including one of the groups of decellularized microparticles of FIG. 2B.

More specifically, as depicted in FIGS. 2A and 2C and described in more detail below, the method 10 shown in FIG. 1 can be carried out using cartilage as the biological tissue and collagen as the curable medium. Additionally, as illustrated by FIGS. 2B, 3A, 3B, 4A-4C, 5A, 5B, 6A, 6B, and 7A-7C and described in more detail below, various medium-microparticle composite matrix systems produced by the method 10 can be used to investigate the effects of a native tissue microenvironment on the differentiation and resulting properties of generated tissue.

FIG. 2A depicts a method 102 of decellularizing cartilage microparticles. Cartilage tissue 100 is provided. For example, the cartilage tissue 100 can be sourced from market weight porcine tissue (at least 200 separate animals) within 48 hours of slaughter and harvested by exposure of knee joint space and scalpel removal of cartilage tissue with care to not include any calcified tissue. The harvested tissue is immediately frozen at −80° C. until further processing. The tissue 100 is devitalized via pulverization in a liquid nitrogen magnetic freezer mill (step 104) to form devitalized microparticles 108. The devitalized microparticles are subsequently sorted via a microsieve stack (step 112) and collected to have a distributed particle diameter of 67-500 μm (35-230 standard mesh size). The devitalized microparticles can alternatively be sorted and collected to have a distributed particle diameter of between 1 nm and 200 μm. More specifically, the microparticles can have a distributed particle diameter of between 1 nm and 63 μm, between 63 μm and 250 μm, between 250 μm and 500 μm, between 500 μm and 710 μm, or between 710 μm and 1000 μm. Resulting sorted, size-controlled cartilage microparticles 116 are decellularized in 2% sodium dodecyl sulfate for 6 hours to remove cellular and genetic material to specifications (step 120). At least a portion of the decellularized cartilage microparticles 124 are then 3× rinsed in ddH$_2$O, flash frozen in LN$_2$, and lyophilized.

As noted above, the decellularized cartilage microparticles 124 contain mature, healthy cartilage ECM, which promotes integration with target cartilage tissue, but the cellular and genetic material have been removed, which prevents an immunogenic response when the microparticles are ultimately implanted into the body.

To examine the potential contribution of the many physicochemical components of native tissue, the cartilage microparticles can be used to form four groups having various physiological properties. To form the groups of cartilage microparticles, a portion of the cartilage microparticles can be reduced using previously established Gu.HCl-based procedures. As shown in FIG. 2B, these four groups include: unmodified decellularized cartilage microparticles (DCM microparticles or DCM) 124, Gu.HCl extracted insoluble component of decellularized cartilage microparticles (IDCM microparticles or IDCM) 128, Gu.HCl extracted soluble component of decellularized cartilage microparticles (SDCM microparticles or SDCM) 132, and reconstituted components of decellularized cartilage microparticles (RDCM microparticles or RDCM) 136.

As shown in FIG. 2B, to form the four groups of cartilage microparticles, a portion of the lyophilized DCM microparticles 124 is subjected to reduction via treatment in 4M Gu.HCl with 1% protease inhibitor and 25 mM EDTA under rotation for 48 hours at 4° C. (step 140). After Gu.HCl treatment, samples are centrifuged at 1600×g for 15 minutes, the supernatant is collected in a separate container for soluble protein extraction, and the insoluble pellet is washed in ddH$_2$O, flash frozen in liquid nitrogen, and lyophilized for the extraction of IDCM microparticles 128. The supernatant is precipitated in 100% EtOH overnight at −20° C., washed with 100% EtOH, and subsequently dialyzed against ddH$_2$O at 25° C. to completion. Dialyzed solution is flash frozen in liquid nitrogen and lyophilized forming a soluble reduction component of the decellularized cartilage microparticles (SDCM microparticles) 132. Gu.HCl reduction can be verified via SDS-PAGE analysis. RDCM microparticles 136 are formed by mechanically mixing the soluble and insoluble reduction components (step 144).

Collagen-cartilage microparticle matrix composite systems of each of the four groups of cartilage microparticles can be formed via encapsulation and densification of the cartilage microparticles within polymerized collagen matrices. More specifically, DCM microparticles are mixed into the collagen at 1% w/v (10 mg/mL) initial concentration and then subject to matrix densification via plastic compression (described in more detail below) to a strain of 90% to effectively increase the DCM microparticle concentration to approximately 10% w/v, approaching physiological levels. As used herein, the term "physiological levels" means levels that are naturally present in the native target tissue. These levels can be chosen, for example, as a result of a series of pilot studies investigating both initial microparticle density and size. Initial densities of 2% w/v and greater lead to significant shearing within the construct when compressed, compromising the structural integrity of the whole composite. Similarly, particles sized larger than 500 μm were found to reach percolation and begin shearing the composite at lower strain than particles sized <500 μm. Similarly, IDCM and SDCM microparticles are mixed with the collagen at appropriate ratios as measured from the reduction (0.8% w/v for IDCM, 0.2% w/v for SDCM) and similarly compressed. RDCM microparticle composites are formed by mechanically mixing the soluble and insoluble reduction components to at the same previously described concentrations (0.8% w/v IDCM+0.2% w/v SDCM→1% w/v RDCM) and similarly compressed.

As shown in FIG. 2C, each of the microparticle components is mixed with a medium to form a microparticle-medium composite 148, the microparticle-medium composite 148 is placed in a mold 150 and is then cured (step 152) to form the microparticle-medium composite matrix. In the present embodiment, the medium is neutralized type I collagen oligomers (5 mg/mL). In alternative embodiments, however, the microparticle components can be mixed with a different curable medium. In the present embodiment, the mold 150 is rectangular with dimensions 10 mm×5 mm×14 mm. In alternative embodiments, however, the mold can have a different shape and size that is sufficient to contain the microparticle-medium composite 148 and enable curing thereof. In the present embodiment, the medium is cured by polymerization at 37° C. for 30 minutes. In alternative embodiments, however, the medium can be a different medium and/or can be curable by a different process.

After curing, the microparticle-medium composite matrix 154 is placed in a servoelectric mechanical testing system 156 and compressed via confined compression (step 158) to form the microparticle-medium composite matrix system. The microparticle-medium composite matrix 154 can be compressed, for example, to a final strain magnitude of 90% at a strain rate of $0.1\% \text{ s}^{-1}$. In the present embodiment, the microparticle-medium composite matrix 154 is compressed with a porous platen 160 having, for example, a porosity of 15% and a pore size of 35 μm. The porous platen 160 enables fluid, for example, liquid, gas, or colloidal suspension, to flow out of the microparticle-medium composite matrix 154 during compression to increase the density of the microparticles within the medium. In alternative embodiments, however, the samples 154 can be compressed with a different compression member instead of the porous platen 160. Furthermore, the compression member need not be porous, as fluid may also flow between the compression member and the mold during compression.

Once the predetermined density of microparticles within the medium has been reached, the microparticles and medium have formed the composite matrix system 164. The exemplary composite matrix system 164 shown in FIG. 2C has been magnified for viewing. The composite matrix system 164 is a high strength, high density, three-dimensional structure, which can be implanted into the body for integration and tissue generation. The density of microparticles in the microparticle-medium composite matrix system 164 is tunable by controlling the compression of the microparticle-medium composite matrix. The predetermined density of microparticles within the medium is determined by the intended use of the microparticle-medium composite matrix system 164. In the present example, the microparticle-medium composite matrix system 164 is to be implanted into the body to generate articular cartilage tissue. Accordingly, the predetermined density of cartilage microparticles in the cartilage-collagen composite matrix system is that which closely mimics that of native articular cartilage tissue.

Figures 3A, 3B:
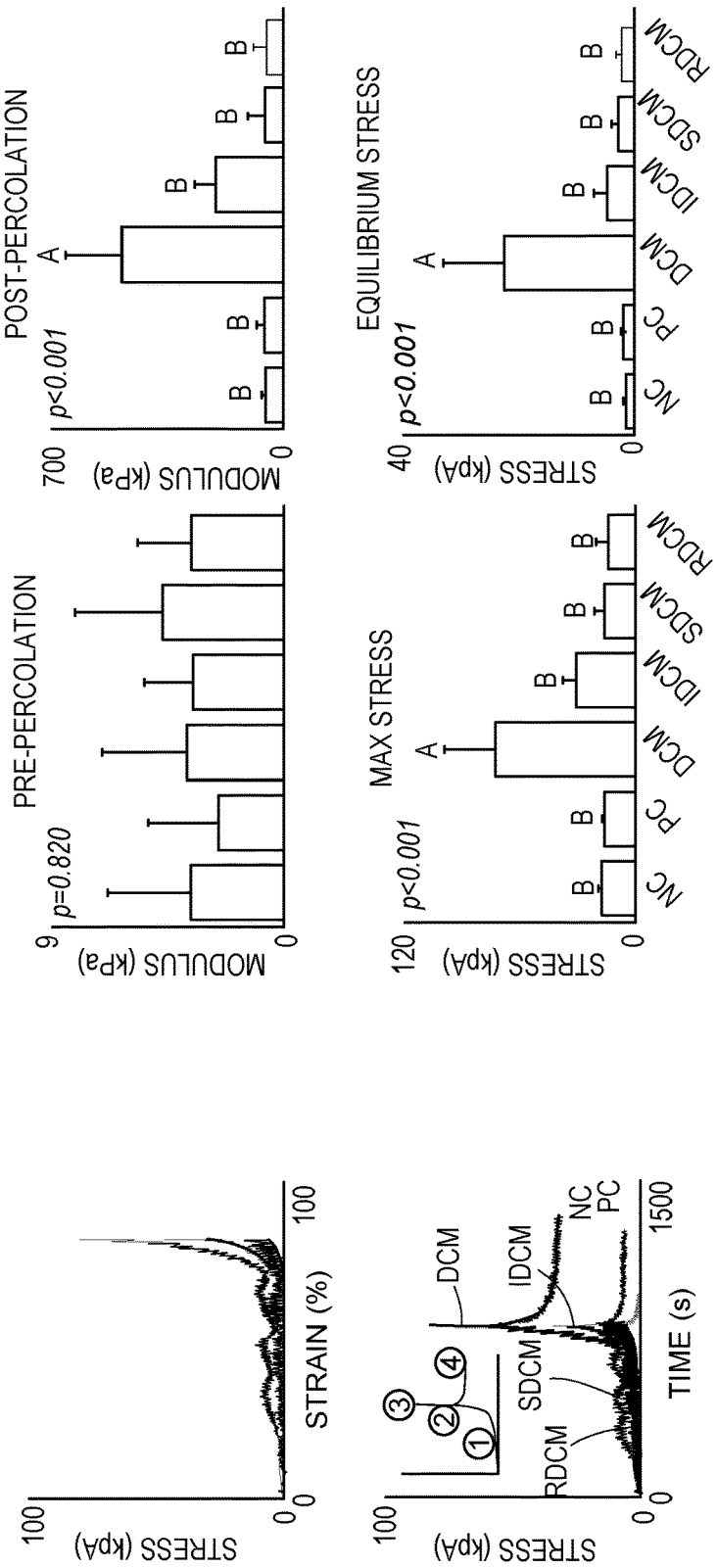
FIG. 3A depicts a mechanical analysis of composite matrices formed using the method of FIG. 2C.
FIG. 3B depicts another mechanical analysis of the composite matrices formed using the method of FIG. 2C.

The method described above further enables testing and investigation of various properties of the microparticle-medium composite matrix to, in part, enable examination of the contribution of the complex native cartilage microenvironment to the induction of chondrogenic differentiation. In particular, during compression (step 158), mechanical responses and properties of the samples 154, including pre-percolation modulus, post-percolation modulus, and maximum stress, can be measured. As shown in the inset of FIG. 3A, the percolation threshold, indicated by reference numeral 2, is defined as the strain level where the linear modulus of compression suddenly increases, suggesting bulk contact of cartilage microparticles. Compression is additionally held after the test until equilibrium where equilibrium/residual stress is measured.

It is important to note that the soluble components, although lyophilized, are soluble again once introduced to the unpolymerized collagen solution. Therefore, unlike other groups, the SDCM group contains no solid cartilage particulate or microparticles of any sort. To examine the potential leaching of the SDCM component into the media, the SDCM composites can be placed into isotonic PBS for 1 week, sampling at 3 and 7 days with fluid change at each sampling point. Leached material can be measured via both DMMB assay and A280 protein spectroscopy.

The ultrastructure of cartilage and collagen components can be assessed via cryo-SEM, for example, using an Everhart-Thornley (<10,000× magnification) or immersion lens (>10,000× magnification) detector. For example, samples are frozen in critical state liquid nitrogen, fractured to the imaging plane, and sublimated for 13 minutes to reveal collagen ultrastructure. Images are acquired at magnifications between 300× and 40,000× to visualize gross structure and specific fibril areas within cartilage microparticles and the collagen matrix. Images at 10,000× are obtained at three separate locations to determine the ultrastructural differences between sample groups. Mean fibril thickness, maximum fibril thickness, and fibril area fraction can be quantified and analyzed at three separate locations in both cartilage and collagen regions using the Thickness and Volume Fraction functions in BoneJ, developed to measure these properties in trabecular bone. SEM images are thresholded and binarized prior to analysis. Prior to analysis, BoneJ software can be validated through the development of a custom MATLAB script, outputting artificial fibril networks of specified mean size and distribution.

To examine the signaling potential of the cartilage microparticle composites, low passage human mesenchymal stem cells (hMSCs) can be additionally encapsulated prior to polymerization and compression. Low passage hMSCs, for example less than or equal to passage 5, can be seeded at 1E6 cells mL initial concentration, with an average post-compression concentration of 10E6 cells $mL^{-1}$. A total of 6 groups (n=6 for each) are initiated for a 2 week differentiation study examining the chondrogenic induction potential of cartilage microparticles within a collagen matrix. The negative control (NC) group is composed of densified collagen in the absence of any microparticles and cultured in non-differentiating media. Positive controls (PC) are also composed of densified collagen in the absence of microparticles but cultured in chondrogenic induction media containing TGF-β3, the current gold standard for chondrogenic differentiation induction. Four experimental groups are additionally cultured using cartilage microparticles as previously described (DCM, IDCM, SDCM, and RDCM) in non-inducing media. Media is exchanged every two days. At the conclusion of the study, four samples from each group of six can be utilized for quantitative polymerase chain reaction (qPCR) assessment while two samples are immediately fixed in 4% paraformaldehyde at 4° C. overnight and sent for histological processing (hematoxylin and eosin and safranin-o). Prior to separation, samples can be measured for cell-mediated contraction in the length and width dimensions utilizing a dissection microscope backed by a grid of known spacing of, for example, 2.1 mm Total ribonucleic acid (RNA) isolation can be performed using the Aurum Total RNA Mini Kit. Collagen matrices are homogenized and cleaned from protein using two rounds of chloroform precipitation. Total RNA is reverse transcribed into complementary deoxyribonucleic acid (cDNA) using a thermocycler, and Quantitative Real-Time PCR is performed using SsoAdvanced SYBR Green Supermix and the CFX96 Touch adthermocycler. Amplification curves can be analyzed via sigmoidal curve fitting analysis.

A variety of genes can be investigated for hMSC differentiation. For all samples, GAPDH is utilized as the housekeeping gene. Known chondrocyte (ACAN, COL3A1, COLX, and SOX9), myoblast (MYOD1, PAX7, VIM), neuron (GFAP, MAP2), adipocyte (LEP, PPARγ), and osteocyte (BGLAP, SPP1, COL2A2) differentiation genes (shown in the Table below) can be measured for all samples, including undifferentiated hMSCs. The Table includes a list of qPCR primers, associated proteins, and reference sequence numbers.

| Protein/Gene | Label | Seq. Listing ID No. | Primers from 5'-3' | Length | Amplicon | Exon Junction | isotypes | refseq# |
|---|---|---|---|---|---|---|---|---|
| GAPDH glyceraldehyde-3-phosphate dehydrogenase | GAPDH-F | 1 | AAATCAAGTGGGGCGATGCT | 20 | 86 | E3 | all (4) | NM_001256799.2 |
| | GAPDH-R | 2 | CAAATGAGCCCCAGCCTTCT | 20 | | E3/4 | | |
| ACAN Aggrecan | ACAN-F | 3 | CACCTGAGCAGCATCGTCAC | 20 | 145 | E13 | all (2) | NM_001135.3 |
| | ACAN-R | 4 | GCCAGTTCTCAAATTGCATGG | 21 | | E14/15 | | |
| COL2A2 Collagen 1 | COL2A2-F | 5 | GGCTGAGAGGTAGTCCTGGT | 20 | 132 | EX/X + 1 EX + 2 | None | NM_000089.3 |
| | COL2A2-R | 6 | GGCGACCAGCATCTCCATTA | 20 | | | | |
| COL3A1 Collagen 2 | COL3A1-F | 7 | CTGTCCTCTGCGACGACATA | 21 | 136 | E2 | None | NM_001844.4 |

-continued

| Protein/Gene | Label | Seq. Listing ID No. | Primers from 5'-3' | Length | Amplicon | Exon Junction | isotypes | refseq# |
|---|---|---|---|---|---|---|---|---|
| | COL3A1-R | 8 | TTCTGTCCCT TTGGTCCTGG T | 21 | | E3/4 | | |
| COLX Collagen 10 | COLX-F | 9 | CAGCACGCAG AATCCATCTG A | 21 | 137 | E1/2 | None | NM_000493.3 |
| | COLX-R | 10 | TGTTGGGTAG TGGGCCTTTT | 20 | | E2 | | |
| GFAP glial fibrillary acidic protein | GFAP-F | 11 | AGAACCGGAT CACCATTCCC | 20 | 98 | E6/7 | Var 1 | NM_002055.4 |
| | GFAP-R | 12 | CCTCTTGAGG TGGCCTTCTG | 20 | | E8 | | |
| LEP Leptin | LEP-F | 13 | CATTTCACAC ACGCAGTCAG T | 21 | 179 | E2/3 | None | NM_000230.2 |
| | LEP-R | 14 | GGTTCTCCAG GTCGTTGGAT | 20 | | E3 | | |
| MAP2 microtubule-associated protein 2 | MAP2-F | 15 | TTACCACTTC CTTGAATAGT TGCAG | 25 | 219 | E3/4 | all (5) | NM_031845.2 |
| | MAP2-R | 16 | ATGTGAGTGT GCAGATGCCT | 20 | | E4 | | |
| BGLAP Osteocalcin, bone gamma-carboxyglutamic acid-containing protein | BGLAP-F | 17 | ATGAGAGCCC TCACACTCCT | 20 | 117 | E1 | None | NM_199173.4 |
| | BGLAP-R | 18 | CTTGGACACA AAGGCTGCAC | 20 | | | | |
| SPP1 Osteopontin, secreted phosphoprotein 1 | SPP1-F | 19 | ACCTGACATC CAGTACCCTG A | 21 | 133 | E6/7 | all (5) | NM_001040058.1 |
| | SPP1-R | 20 | ACGGCTGTCC CAATCAGAAG | 20 | | E7 | | |
| PPARG mRNA-peroxisome proliferator-activated receptor gamma | PPARG-F | 21 | GCAATCAAAG TGGAGCCTGC | 20 | 183 | E3 | all (4) | NM_015869.4 |
| | PPARG-R | 22 | TCTCCGGAAG AAACCCTTGC | 20 | | E3/4 | | |
| SOX9 SRY (sex determining region Y)-box 9 | SOX9-F | 23 | GCTCTGGAGA CTTCTGAACG A | 21 | 132 | E1/2 | None | NM_000346.3 |
| | SOX9-R | 24 | CCGTTCTTCA CCGACTTCCT | 20 | | E2 | | |

All samples are normalized to the housekeeping gene and further normalized to the identical cell line gene expression prior to the start of the study, where the cells expressed surface markers for undifferentiated hMSCs, to investigate cell differentiation as a result of the different microenvironments presented (cartilage microparticle groups). All primers are specific for all known isotypes and are separated by at least one intron or span an exon-exon junction, if splicing information is available.

Mechanical, ultrastructure, and cell-mediated contraction data can be analyzed via one-way ANOVA with cartilage microparticle treatment (PC, NC, DCM, IDCM, SDCM, and RDCM) as the main effect. Post-hoc analyses can be performed using Tukey's pairwise analysis with 95% confidence. qPCR data can be analyzed via one-way ANOVA with cartilage microparticle treatment as the main effect, and measurements from the undifferentiated hMSCs are included in the analysis. Post-hoc analyses for qPCR data can be analyzed via Dunnett's test and compared to a control level of the gene expression values for undifferentiated hMSCs.

Exemplary results of the above described testing of cartilage-collagen matrices show that microparticles increase composite mechanical properties via percolation. As shown in FIGS. 3A and 3B, the mechanical properties of the composite matrices are dependent on the cartilage microparticle groups. These groups include the otherwise unmodified decellularized cartilage microparticles (DCM), the insoluble product of the guanidine treatment to cartilage microparticles (IDCM), the soluble product of the guanidine treatment to cartilage microparticles (SDCM), and the reconstitution of the two guanidine products (IDCM+SDCM=RDCM). Additionally, positive and negative control groups (PC and NC, respectively) were included for cellular analysis. Both PC (with TGF-β3 supplement) and NC (without supplement) samples were composed of polymerized type I collagen matrices without the inclusion of any native cartilage component.

The linear compression modulus at low strain (pre-percolation) was not statistically dependent on the cartilage microparticle treatment (p=0.820). At high strain, however, near the end of the densification regime, the linear modulus of compression was highly dependent on cartilage microparticle treatment (p<0.001), where samples with the unreduced microparticles (DCM group) had a significantly higher linear modulus compared to other groups. It is likely that the percolation threshold was met for these samples, where the previously suspended particles reached continuous contact throughout the composite matrix, allowing the mechanical properties of microparticles to contribute on a bulk scale. Similarly, max stress and equilibrium stress were found to be dependent on cartilage microparticle groups (p<0.001 for both), where the unreduced DCM group exhibited higher max stress and equilibrium stress.

Notably, composite matrices using the reduced soluble component (SDCM and RDCM groups) were much more difficult and fragile to handle. Post-compression, splitting and fraying of both composites was observed, such that the geometric integrity of the matrices were not intact, where all other samples were easily handled and exhibited geometric integrity throughout compression and transfer processes. As a result, the maintenance of the soluble portion was measured through dimethylmethylene blue (DMMB) analysis in the composite matrices to ensure leaching did not occur in the short term. A one-week study showed readings in the surrounding culture media below the noise level for DMMB colorimetric and 280 nm absorbance analysis at 4 and 7 days, indicating that no soluble cartilage microparticle (SDCM) leaching was occurring.

Densification of the composite matrices enables tuning the final concentration of cartilage microparticles. Interestingly, all samples reached the percolation threshold, wherein the macro-scale structure of the composite matrix was compacted to a point where continuous contact between particles occurred throughout the bulk of the matrix, as apparent by the transition in mechanical properties to the much higher properties of the cartilage microparticles via stress shielding to the collagen network. Since this effect was not seen in the control samples or previous densification work, it is likely that the percolation occurred between cartilage microparticles, and not as an effect of percolation in the surrounding collagen matrix. Composite matrices were able to be formed at a range of 1-4% of extracellular matrix components (wet weight), at the range, and exceeding, that of native cartilage. However, as noted above, higher densities of microparticles led to fragmenting and a lack of structural integrity of the bulk matrix, likely due to failure of the interstitial collagen matrix due to loading or shearing between cartilage microparticles.

Figure 4A:
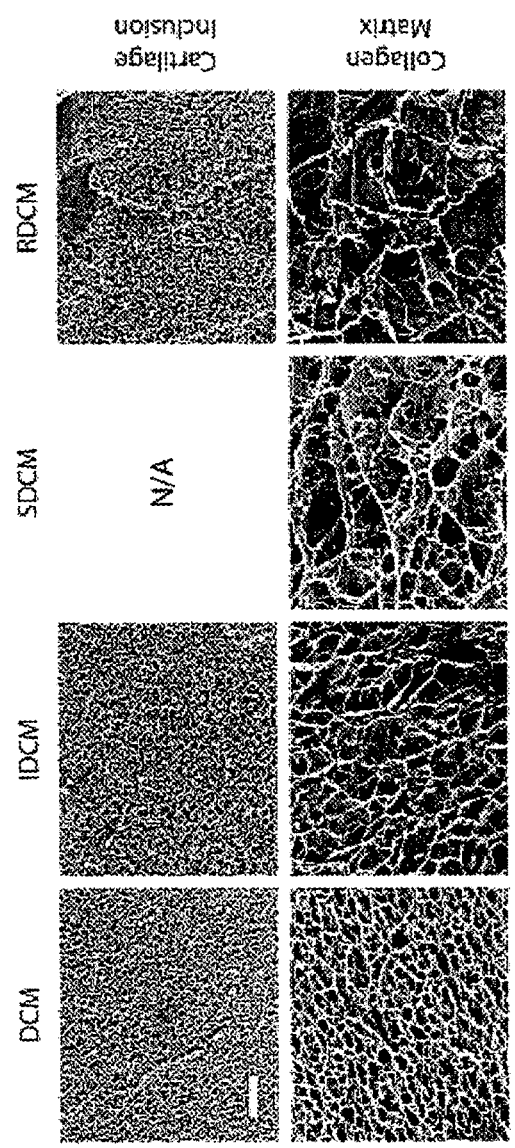
FIG. 4A depicts cryo-SEM images of composite matrices formed using the method of FIG. 2C.
Figure 4B:
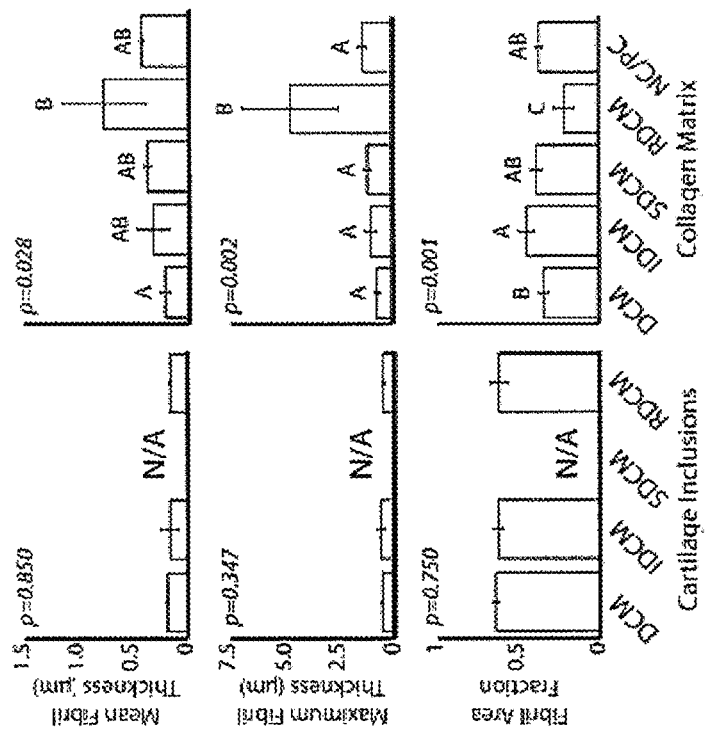
FIG. 4B depicts a quantitative analysis of the SEM images of FIG. 4A.

The mechanical response of the composite matrices was found to be highly dependent on microparticle group, where the highest mechanical response was seen in the unmodified DCM group, with all collagen-GAG interactions inherent in the native cartilage present. The IDCM group, in absence of the covalently bound GAGs, showed a statistically similar mechanical response to collagen-only NC and PC samples, consistent with previous literature where GAGs are implicated as the primary contributor to cartilage compressive properties. However, all differences in mechanical response were seen at high strain in the compression regime, past the percolation threshold (FIG. 3A) where cartilage microparticle mechanics dominated. At lower strain levels, linear moduli between samples were not statistically different, as the strain was likely localized to the surrounding collagen matrix. Further, samples which include the reduced, soluble GAG component (SDCM and RDCM) were found to have much lower mechanical properties and additionally had little structural integrity and were difficult to handle, suggesting that the soluble GAG component interfered with the fibril structure of the collagen matrix, similar to what has been reported previously Exemplary results of the above described testing of cartilage-collagen matrices also show that isolated proteoglycan components alter collagen fibril morphology. As shown in FIG. 4A, cryo-SEM analysis revealed differences in matrix fibril morphology as a result of compression across various cartilage microparticle treatments. As shown in FIG. 4B, measurements of cartilage microparticles showed no significant difference between DCM, IDCM, and RDCM groups in mean fibril thickness (p=0.850), maximum fibril thickness (p=0.347), and fibril area fraction (p=0.750). The cartilage matrix, however, was impacted by the various microparticles. Mean fibril thickness and maximum fibril thickness was significantly higher in RDCM samples (p=0.028 and p=0.002, respectively). As a likely result, fibril area fraction was significantly lower in RDCM samples (p=0.001).

Figure 4C:
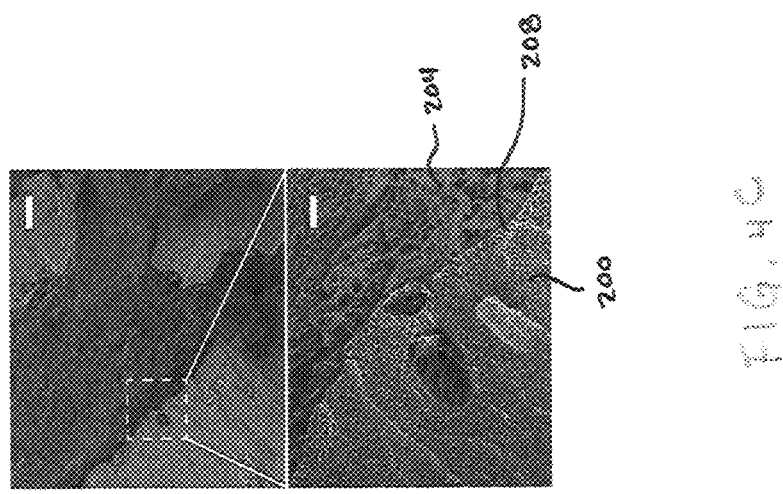
FIG. 4C depicts an interface between the materials of a composite matrix formed using the method of FIG. 2C.

As shown in FIG. 4C, SEM analysis qualitatively showed porosity and density differences between the cartilage microparticles 200 and the surrounding cartilage matrix 204, as well as the interface 208 between them. Qualitative examination of the DCM, IDCM, and RDCM groups showed cartilage microparticles characterized by high-density fibril regions and empty lacunae of the former chondron complex. The interface 208 between the microparticles 200 and the collagen matrix 204 showed greater porosity and aligned fibril regions, suggesting shear effects between the cartilage microparticles and collagen matrix during compression.

Ultrastructural analysis revealed conservation of porosity and fibril characteristics within cartilage microparticles, including chondron lacunae, which was unaffected by Gu.HCl reduction of GAGs. Interestingly, this is converse to previous reports utilizing Gu.HCl, which were shown to increase the porosity of cartilage tissue. Despite the changes in mechanical properties and structural integrity, SDCM samples did not show significant changes in fibril morphology. The collagen matrix only exhibited changes in fibril morphology in the RDCM group. This was likely due to the decreased integrity of the collagen matrix induced by the soluble GAG extract coupled with shearing due to cartilage microparticle interaction beyond the post-percolation threshold. The reduced integrity of the collagen matrix was likely caused by the interaction between the soluble proteoglycan component and the collagen fibrils, as mentioned previously.

Figure 5B:
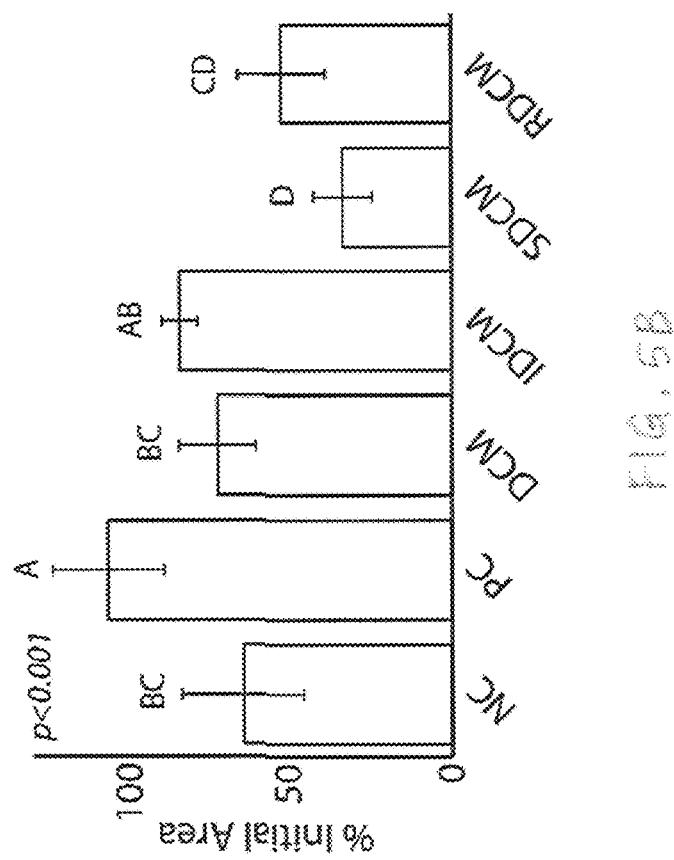
FIG. 5B depicts a quantitative analysis of the physical samples of FIG. 5A.
Figure 5A:
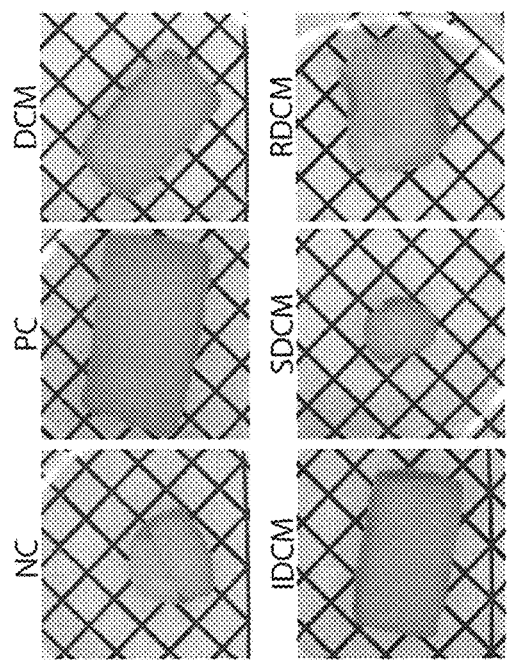
FIG. 5A depicts physical samples of composite matrices formed using the method of FIG. 2C.

Exemplary results of the above described testing of cartilage-collagen matrices also show that microparticles inhibit bulk cell-mediated contraction. As shown in FIGS. 5A and 5B, six sample groups were included for investigation of cellularized matrices. As in the mechanical analysis, DCM, IDCM, SDCM, and RDCM groups were produced as explained above. Further, positive control (PC) and negative control samples (NC) were included for analysis and were composed of cell encapsulated type I collagen matrices cultured in chondrogenic inductive (PC) and non-inductive (NC) media. Qualitative and quantitative analysis of the cellularized composite matrices at two weeks showed significant differences in morphology due to cell-mediated contraction. PC, DCM, and IDCM groups were shown to have the lowest cell-mediated contraction ($p<0.001$). In most of the groups with lower equilibrium mechanical properties (NC, SDCM, RDCM), significant deformation was observed both qualitatively (FIG. 5A) and quantitatively (FIG. 5B).

Cell-mediated contraction was clearly mitigated in PC, DCM, and IDCM samples, where all other samples had large deformations in bulk morphology. As the culture conditions for the PC group were pro-chondrogenic, it is likely that slowed metabolic rate of the cells account for the lack of cell-mediated contraction. Further, it is possible that the pro-chondrogenic media inhibited fibroblast differentiation of the cells, further preventing cell-mediated contraction. For DCM and IDCM samples, the only difference in culture conditions versus negative controls, which did show large deformations, was the presence of the solid cartilage microparticles. This suggests that the composite mechanical structure of the DCM and IDCM particles either mechanically inhibited cell mediated contraction, induced a phenotype in the stem cells that mitigated contractile forces, or a combination thereof. This result is also consistent with previous work showing increased mechanics leading to mitigated cell-mediated contraction. However, when the isolated soluble extract was presented to the construct (SDCM and RDCM groups), which has already been shown to alter mechanical properties and fibril morphology, cell-mediated contraction and construct deformation occurred on a level consistent with the negative control samples, even in the presence of physical microparticles (the IDCM component of the RDCM group). It is likely that, even in the presence of solely fibroblast-like cells, the solid microparticles of the DCM and IDCM groups contributed to the bulk of the resistance to cell-mediated contraction. Further, the maintenance of geometry suggests minimized disruption of the composite structure, such that the type I collagen matrix maintained a complete network surrounding the compressed microparticles. SDCM and RDCM groups, however, exhibited collagen matrix fraying, suggesting a disruption of the complete network structure, further supported by the diminished mechanical properties in these groups.

Figure 6A:
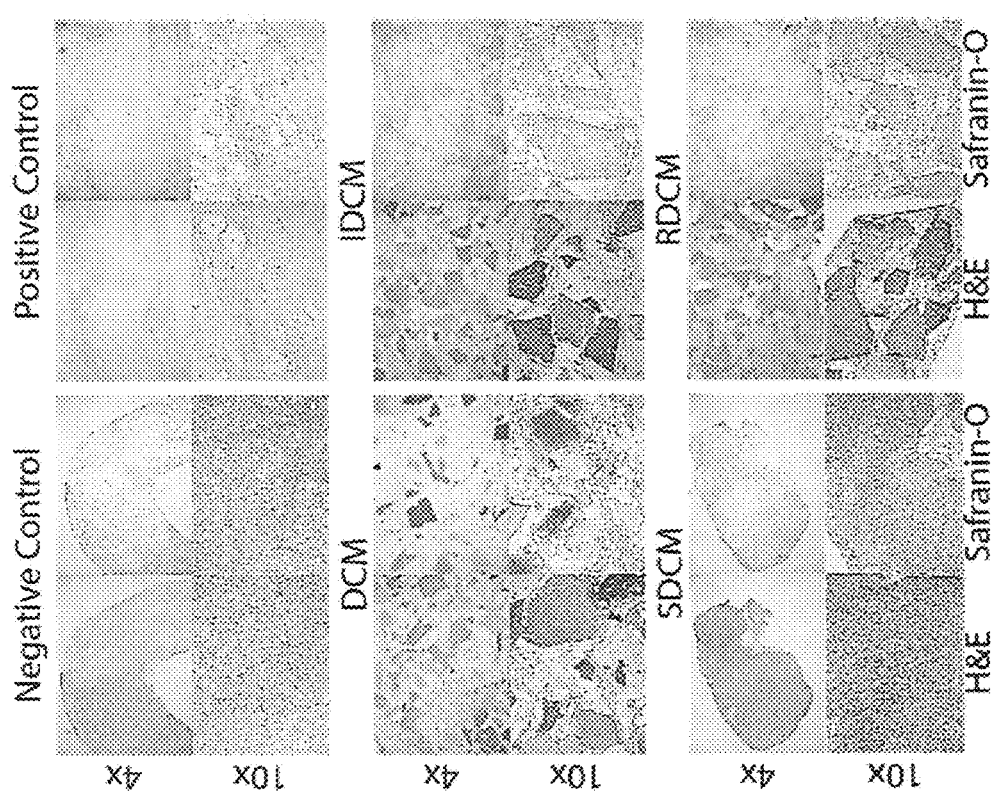
FIG. 6A depicts histological samples of composite matrices formed using the method of FIG. 2C at 4× and 10× magnification
Figure 6B:
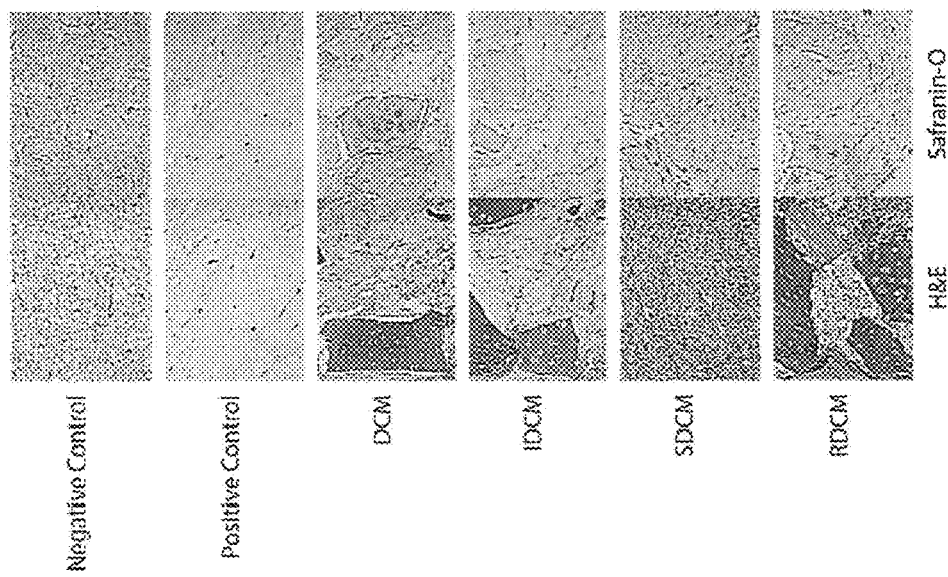
FIG. 6B depicts the histological samples of FIG. 6A at 20× magnification.

Unmodified and insoluble cartilage microparticles showed cellular infiltration and proteoglycan production. As shown in FIGS. 6A and 6B, histological analysis revealed the morphological and biochemical differences between each of the treatment groups. Negative control samples showed distorted morphology of the matrix, but an intact collagen structure via hematoxylin and eosin (H&E) stain. Safranin-O stain showed no presence of proteoglycans or the formation of articular cartilage tissue. Both stains showed elongated cell bodies homogenously distributed throughout the sample. Positive control samples, alternatively, showed via H&E stain no distortion in morphology, but similar cell body elongation and no presence of articular cartilage formation, despite the presence of chondro-inductive growth factors (TGF-β3). DCM samples showed an even distribution of cartilage microparticles throughout the collagen matrix and clear safranin-o staining of characteristic cartilage tissue. Interestingly, cartilage microparticles that maintained red safranin-o staining also showed cellular infiltration of cartilage lacunae, where those that showed little cell infiltration consistently showed little cartilage staining.

As expected, IDCM groups, depleted of GAGs via Gu.HCl reduction, showed no red safranin-o staining of the cartilage microparticles, while showing similar distribution and size within the composite matrix to the DCM group. Interestingly, those cartilage microparticles that showed cellular infiltration additionally showed mild red safranin-o staining near the lacunae edges. Cells not within the microparticles showed cellular elongation. SDCM groups, as noted previously, did not contain any solid cartilage pieces but contained the soluble reduction from the Gu.HCl treatment. As a result, no cartilage microparticles are present and similar elongated cell bodies were seen. Similar to as previously described, SDCM samples were not structurally intact and did not exhibit any cartilage specific staining. RDCM samples, similar to both IDCM and SDCM, did not exhibit high levels of cartilage specific safranin-o staining, but did maintain the cartilage microparticle structures similar to DCM and IDCM. However, as noted above, RDCM samples showed low structural integrity and similarly showed cell body elongation in the interstitial spaces between cartilage microparticles.

The histological analysis showed cellular infiltration in chondron lacunae and maintenance of positive cartilage safranin-o staining for DCM samples, similar to previous research. Additionally, cellular infiltration into chondron lacunae was apparent in IDCM samples as well. Otherwise, all cells in the collagen matrix and in other samples exhibited elongated cell bodies. As expected, unmodified DCM samples exhibit positive safranin-o staining where IDCM samples did not due to the Gu.HCl extraction of GAGs. Interestingly, within DCM samples, particles that exhibit less infiltration also show less overall safranin-o staining, suggesting that infiltrated cells contribute to the maintenance of the cartilage microenvironment. Additionally, IDCM particles with infiltrated cells show light safranin-o staining, further supporting possible chondrogenic induction very localized to specific cellular interactions with cartilage microparticles. Further, this may suggest a heightened role of the mechanical and biochemical properties of the collagenous cartilage matrix, and merits further investigation into the manipulation of type II collagen structures to higher physiological relevance to investigate their potential in cartilage regeneration. All other samples, including positive control samples, show little evidence of positive safranin-o staining or chondrogenic cell morphology. As a result, the large majority of the cell population, even in DCM and IDCM samples, do not have contact with the cartilage microparticles and may not receive the signals necessary for chondrogenic induction. This is similar with previous research in this field, where the majority of cells reside in the interstitium between particles with little cartilage positive staining. The small number of cells that do interact with cartilage microparticles show chondrogenic morphology and mitigation of local GAG degradation.

Figure 7A:
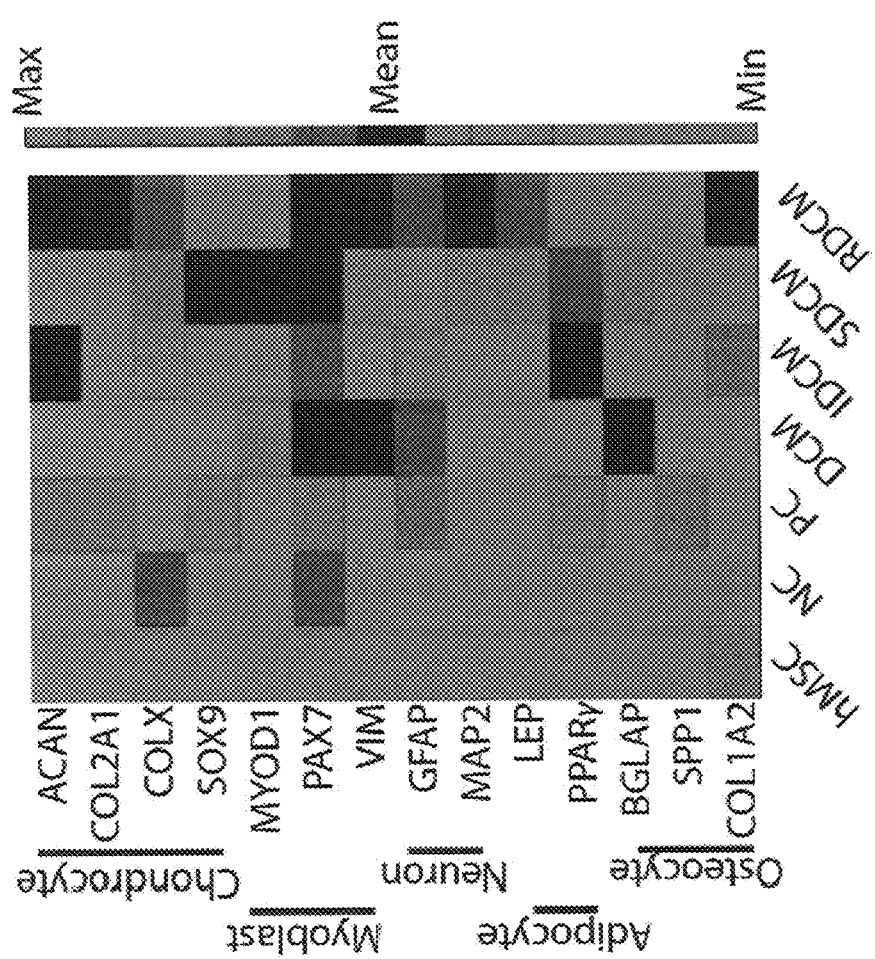
FIG. 7A depicts a heat map of a gene array of composite matrices formed using the method of FIG. 2C.
Figure 7B:
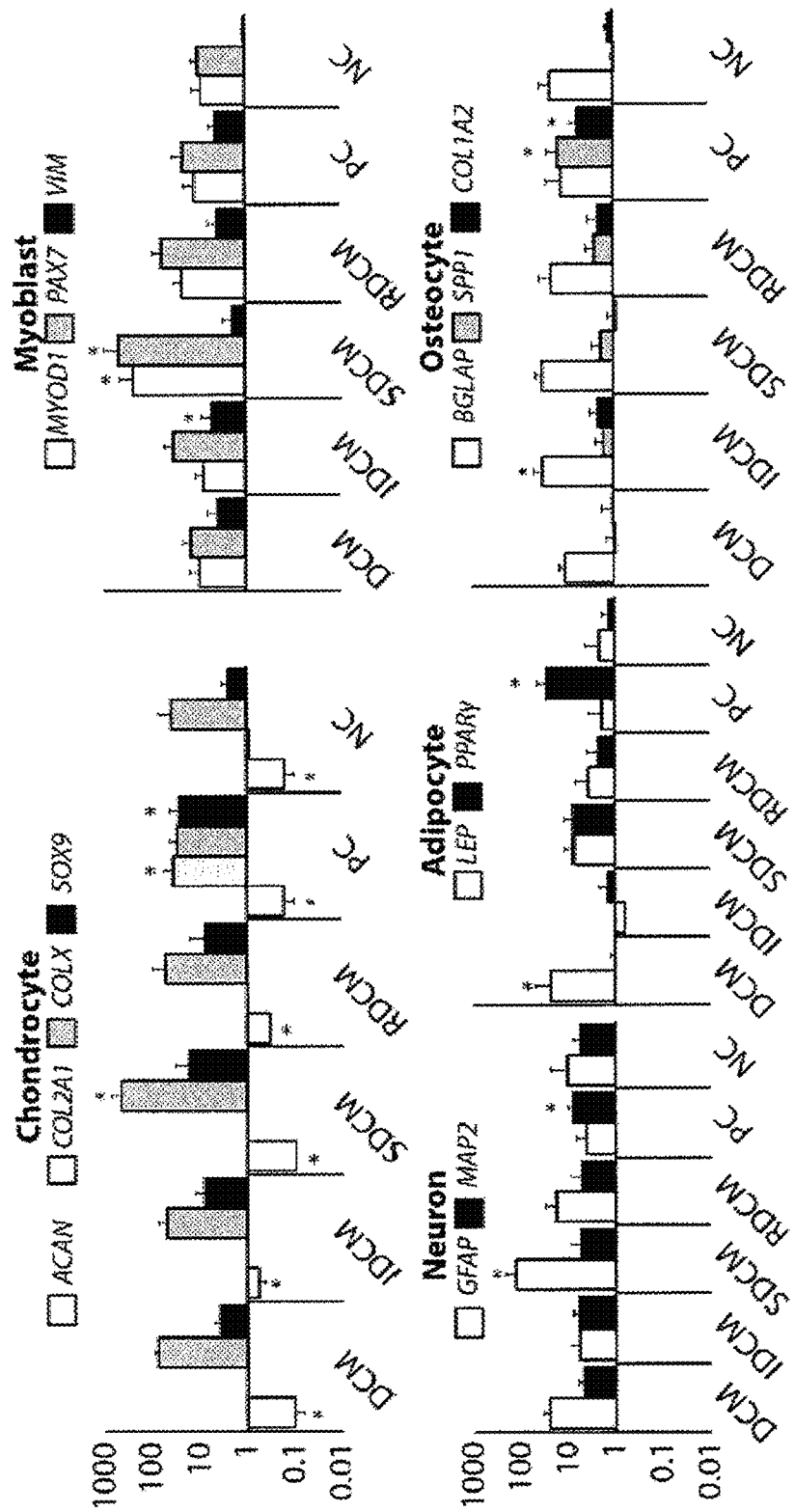
FIG. 7B depicts a quantitative analysis of the gene array of FIG. 7A.

The exemplary results of the above described testing of cartilage-collagen matrices also show that local MSC differentiation occurred in cells in contact with microparticles. As shown in FIGS. 7A and 7B, gene expression analysis showed varying stem cell differentiation as a result of treatment group. Across groups, significant gene differences were seen for: cartilage markers-ACAN ($p<0.001$), COL3A1 ($p<0.001$), COLX ($p<0.001$), and SOX9 ($p=0.002$); myoblast markers-MYOD1 ($p<0.001$), PAX7 ($p=0.027$), and VIM ($p=0.040$); neuron markers-GFAP ($p<0.001$) and MAP2 ($p=0.057$); adipocyte markers-LEP ($p=0.035$) and PPARγ($p<0.001$); and osteocyte markers-SPP1 ($p<0.001$), COL2A2 ($p<0.001$) and BGLAP ($p=0.057$).

When compared to undifferentiated hMSCs as a control, all samples downregulated ACAN ($p<0.05$) while COL3A1 and SOX9 were only significantly upregulated in positive controls ($p<0.05$). COLX, a cartilage hypertrophy indicator, was significantly upregulated in SDCM samples. Myoblast markers were significantly upregulated in IDCM (VIM, p<0.05) and SDCM (MYOD1 and PAX7, p<0.05 for both). Neuron markers were upregulated in SDCM (GFAP, p<0.05) and PC (MAP2, p<0.05) samples. Adipocyte markers were upregulated in DCM (LEP, p<0.05) and PC (PPARγ, p<0.05) samples. Osteocyte markers were upregulated in IDCM (BGLAP, p<0.05) and PC (SPP1 and COL2A2, p<0.05 for both) samples. Additionally, positive control samples exhibited upregulation in MAP2, PPARγ, SPP1, and COL2A2 (p<0.05 for all).

A high percentage of the cell population was found to be suspended in the collagen matrix without interaction with cartilage microparticles. A rounded, chondrogenic morphology was not observed in these cells, and a large number of cells were expected to show differentiation in a non-chondrogenic pathway. Real time quantitative PCR supports this hypothesis, showing no significant upregulation of cartilage markers in any sample except the positive control sample. This is converse to previous reports, although this method did not include looking at markers other than chondrogenic genes.

The data suggests that the undifferentiated cells respond to direct interaction with the critical signals (in the case of positive controls, the presence of diffused TGF-β3), and not just the presence of the microparticles. However, samples containing the soluble extract (SDCM and RDCM) might be expected to contain enough diffused GAGs to interact globally with encapsulated cells. It is possible that the signal provided by the soluble extract is not sufficient to induce differentiation in the undifferentiated stem cell line. Additionally, it is likely that significant GAG degradation is occurring over time, as seen in DCM samples, as opposed to the positive control, which is consistently supplemented with TGF-β3.

Interestingly, the positive control samples also exhibit upregulation in neuron, adipocyte, and osteocyte markers, though not to the level and consistency as chondrocyte markers. SDCM, in the absence of interaction with the solid cartilage microparticles structure, showed hypertrophic chondrocyte markers (COLX) and showed significant myoblast differentiation.

It appears as though, while not globally inducing chondrocyte differentiation, the presence of microparticles in DCM and IDCM samples mitigated differentiation down non-chondrogenic pathways. Previous studies similar to these suggest that, given more time, global chondrogenic differentiation would occur in DCM and potentially IDCM samples. This suggests an importance of the physicochemical structure of native cartilage tissue in the differentiation and maintenance of the chondrocyte phenotype. Further investigation of this cell-matrix interaction with the unmodified (DCM) and reduced (IDCM) and the potential for engineering a similar system with an adequate type II collagen system.

The foregoing detailed description of one or more embodiments of a method of making a composite matrix system having a predetermined density of biological tissue microparticles has been presented herein by way of example only and not limitation. It will be recognized that there are advantages to certain individual features and functions described herein. Moreover, it will be recognized that various alternatives, modifications, variations, or improvements of the above-disclosed embodiments and other features and functions, or alternatives thereof, may be desirably combined into many other different embodiments, systems, or applications. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the embodiments contained herein.

What is claimed is:

1. A method of making a composite matrix system having a predetermined density of biological tissue microparticles, comprising:
   sorting biological tissue microparticles into a plurality of groups of biological tissue microparticles having different sizes;
   selecting at least one of the groups of sorted tissue microparticles based on the predetermined density of biological tissue microparticles;
   decellularizing the at least one group of selected tissue microparticles to remove cellular and genetic material;
   mixing the decellularized tissue microparticles into a collagen medium to form a medium-tissue microparticle composite; and
   plastically compressing the medium-tissue microparticle composite to form the composite matrix having the predetermined density of biological tissue microparticles;
   placing the medium-tissue microparticle composite into a mold prior to plastically compressing the medium-tissue microparticle composite; and
   curing the medium-tissue microparticle composite in the mold prior to plastically compressing the medium-tissue microparticle composite.

2. The method of claim 1, further comprising: forming the tissue microparticles by pulverizing biological tissue prior to sorting the tissue microparticles.

3. The method of claim 1, wherein: plastically compressing the medium-tissue microparticle composite includes removing fluid from the cured medium-tissue microparticle composite.

4. The method of claim 3, wherein: removing fluid from the cured medium-tissue microparticle composite includes compressing the cured medium-tissue microparticle composite in the mold with a compression member.

5. The method of claim 3, wherein: removing fluid from the cured medium-tissue microparticle composite includes compressing the cured medium-tissue microparticle composite with a porous platen.

6. The method of claim 1, wherein: the tissue microparticles are cartilage microparticles.

7. The method of claim 1, wherein: the collagen medium is neutralized type I collagen oligomers.

8. A method of making a biological tissue composite, comprising:

pulverizing biological tissue into tissue microparticles;

sorting the tissue microparticles into a plurality of groups of tissue microparticles having different sizes;

selecting at least one of the groups of sorted tissue microparticles based on a predetermined density of biological tissue microparticles;

decellularizing the at least one selected group of tissue microparticles to remove cellular and genetic material;

mixing the decellularized tissue microparticles into a collagen medium to form a medium-tissue microparticle composite; and plastically compressing the medium-tissue microparticle composite to form a composite matrix having the predetermined density of biological tissue microparticles.

9. The method of claim 8, further comprising: placing the medium-tissue microparticle composite into a mold prior to plastically compressing the medium-tissue microparticle composite.

10. The method of claim 9, further comprising: curing the medium-tissue microparticle composite in the mold.

11. The method of claim 10, wherein: plastically compressing the medium-tissue microparticle composite includes removing fluid from the cured medium-tissue microparticle composite.

12. The method of claim 11, wherein: removing fluid from the cured medium-tissue microparticle composite includes compressing the cured medium-tissue microparticle composite in the mold with a compression member.

13. The method of claim 11, wherein: removing fluid from the cured medium-tissue microparticle composite includes compressing the cured medium-tissue microparticle composite with a porous platen.

* * * * *

SEQUENCE LISTING

<160> NUMBER OF SEQ ID NOS: 24

<210> SEQ ID NO 1
<211> LENGTH: 20
<212> TYPE: DNA
<213> ORGANISM: Homo sapiens

<400> SEQUENCE: 1
aaatcaagtg gggcgatgct                                          20

<210> SEQ ID NO 2
<211> LENGTH: 20
<212> TYPE: DNA
<213> ORGANISM: Homo sapiens

<400> SEQUENCE: 2
caaatgagcc ccagccttct                                          20

<210> SEQ ID NO 3
<211> LENGTH: 20
<212> TYPE: DNA
<213> ORGANISM: Homo sapiens

<400> SEQUENCE: 3
cacctgagca gcatcgtcac                                          20

```
<210> SEQ ID NO 4
<211> LENGTH: 21
<212> TYPE: DNA
<213> ORGANISM: Homo sapiens

<400> SEQUENCE: 4
gccagttctc aaattgcatg g                                    21

<210> SEQ ID NO 5
<211> LENGTH: 20
<212> TYPE: DNA
<213> ORGANISM: Homo sapiens

<400> SEQUENCE: 5
ggctgagagg tagtcctggt                                      20

<210> SEQ ID NO 6
<211> LENGTH: 20
<212> TYPE: DNA
<213> ORGANISM: Homo sapiens

<400> SEQUENCE: 6
ggcgaccagc atctccatta                                      20

<210> SEQ ID NO 7
<211> LENGTH: 21
<212> TYPE: DNA
<213> ORGANISM: Homo sapiens

<400> SEQUENCE: 7
ctgtcctctg cgacgacata a                                    21

<210> SEQ ID NO 8
<211> LENGTH: 21
<212> TYPE: DNA
<213> ORGANISM: Homo sapiens

<400> SEQUENCE: 8
ttctgtccct ttggtcctgg t                                    21

<210> SEQ ID NO 9
<211> LENGTH: 21
<212> TYPE: DNA
<213> ORGANISM: Homo sapiens

<400> SEQUENCE: 9
cagcacgcag aatccatctg a                                    21

<210> SEQ ID NO 10
<211> LENGTH: 20
<212> TYPE: DNA
<213> ORGANISM: Homo sapiens

<400> SEQUENCE: 10
tgttgggtag tgggcctttt                                      20

<210> SEQ ID NO 11
<211> LENGTH: 20
<212> TYPE: DNA
<213> ORGANISM: Homo sapiens

<400> SEQUENCE: 11
agaaccggat caccattccc                                      20
```

<210> SEQ ID NO 12
<211> LENGTH: 20
<212> TYPE: DNA
<213> ORGANISM: Homo sapiens

<400> SEQUENCE: 12
cctcttgagg tggccttctg                                               20

<210> SEQ ID NO 13
<211> LENGTH: 21
<212> TYPE: DNA
<213> ORGANISM: Homo sapiens

<400> SEQUENCE: 13
catttcacac acgcagtcag t                                             21

<210> SEQ ID NO 14
<211> LENGTH: 20
<212> TYPE: DNA
<213> ORGANISM: Homo sapiens

<400> SEQUENCE: 14
ggttctccag gtcgttggat                                               20

<210> SEQ ID NO 15
<211> LENGTH: 25
<212> TYPE: DNA
<213> ORGANISM: Homo sapiens

<400> SEQUENCE: 15
ttaccacttc cttgaatagt tgcag                                         25

<210> SEQ ID NO 16
<211> LENGTH: 20
<212> TYPE: DNA
<213> ORGANISM: Homo sapiens

<400> SEQUENCE: 16
atgtgagtgt gcagatgcct                                               20

<210> SEQ ID NO 17
<211> LENGTH: 20
<212> TYPE: DNA
<213> ORGANISM: Homo sapiens

<400> SEQUENCE: 17
atgagagccc tcacactcct                                               20

<210> SEQ ID NO 18
<211> LENGTH: 20
<212> TYPE: DNA
<213> ORGANISM: Homo sapiens

<400> SEQUENCE: 18
cttggacaca aaggctgcac                                               20

<210> SEQ ID NO 19
<211> LENGTH: 21
<212> TYPE: DNA
<213> ORGANISM: Homo sapiens

<400> SEQUENCE: 19

```
                                    -continued acctgacatc cagtaccctg a                                         21

<210> SEQ ID NO 20
<211> LENGTH: 20
<212> TYPE: DNA
<213> ORGANISM: Homo sapiens

<400> SEQUENCE: 20
acggctgtcc caatcagaag                                           20

<210> SEQ ID NO 21
<211> LENGTH: 20
<212> TYPE: DNA
<213> ORGANISM: Homo sapiens

<400> SEQUENCE: 21
gcaatcaaag tggagcctgc                                           20

<210> SEQ ID NO 22
<211> LENGTH: 20
<212> TYPE: DNA
<213> ORGANISM: Homo sapiens

<400> SEQUENCE: 22
tctccggaag aaaccttgc                                            20

<210> SEQ ID NO 23
<211> LENGTH: 21
<212> TYPE: DNA
<213> ORGANISM: Homo sapiens

<400> SEQUENCE: 23
gctctggaga cttctgaacg a                                         21

<210> SEQ ID NO 24
<211> LENGTH: 20
<212> TYPE: DNA
<213> ORGANISM: Homo sapiens

<400> SEQUENCE: 24
ccgttcttca ccgacttcct                                           20
```